(12) United States Patent
Piombini et al.

(10) Patent No.: US 8,015,857 B2
(45) Date of Patent: Sep. 13, 2011

(54) METHOD FOR MEASURING THE GAS PERMEABILITY OF CONTAINERS AND SEALING MEMBERS IN GENERAL

(75) Inventors: Alessandro Piombini, Porto Azzuro (IT); Mauro Lucchesi, Lucca (IT)

(73) Assignee: Extrasolution S.R.L., Pisa (IT)

( * ) Notice: Subject to any disclaimer, the term of this patent is extended or adjusted under 35 U.S.C. 154(b) by 401 days.

(21) Appl. No.: 12/440,860

(22) PCT Filed: Sep. 10, 2007

(86) PCT No.: PCT/IB2007/002595
§ 371 (c)(1),
(2), (4) Date: Mar. 11, 2009

(87) PCT Pub. No.: WO2008/032170
PCT Pub. Date: Mar. 20, 2008

(65) Prior Publication Data
US 2009/0282900 A1 Nov. 19, 2009

(30) Foreign Application Priority Data

Sep. 12, 2006 (IT) ................. PI2006A0106

(51) Int. Cl.
*G01N 15/08* (2006.01)
(52) U.S. Cl. .............................. 73/38; 702/50
(58) Field of Classification Search .......... None
See application file for complete search history.

(56) References Cited

U.S. PATENT DOCUMENTS

| 3,590,634 A | * | 7/1971 | Pasternak et al. | 374/54 |
| 3,618,361 A | * | 11/1971 | Stephens et al. | 73/38 |
| 5,513,515 A | | 5/1996 | Mayer | |
| 2010/0268488 A1 | * | 10/2010 | Bismarck et al. | 702/50 |

FOREIGN PATENT DOCUMENTS

| WO | 02088657 | 11/2002 |
| WO | 03060485 | 7/2003 |

OTHER PUBLICATIONS

R.W. Balluffi, S.M. Allen, W.C. Carter, "Kinetics of Materials", Dec. 30, 2005, John Wiley & Sons, Hoboken, New Jersey, USA; XP002468865, p. 99-103.

* cited by examiner

*Primary Examiner* — Harshad Patel
(74) *Attorney, Agent, or Firm* — Roylance, Abrams, Berdo and Goodman, L.L.P.

(57) ABSTRACT

A device that carries out a method for measuring permeability to a gas sample through a container (2) comprises an inlet duct for the gaseous carrier, in particular, nitrogen, both as inlet in the container (2) and as inlet in the chamber (1) and out of the container (2) of which permeability has to be measured. The inlet duct that exits in the container (2) comprises two ducts (11 and 8), whereas the inlet duct that exits out of the container (2) comprises two ducts (6 and 7). Such inlet ducts have an origin in common in order to allow the distribution between them of the flow (200) of gas carrier as input. An inlet duct is provided (10) for a test gas flow, such as oxygen, which ends in the duct (7) to be measured, with the gas carrier in the chamber (1). A gas-mass regulator is provided for each inlet duct (5, 4 and 3).

9 Claims, 5 Drawing Sheets

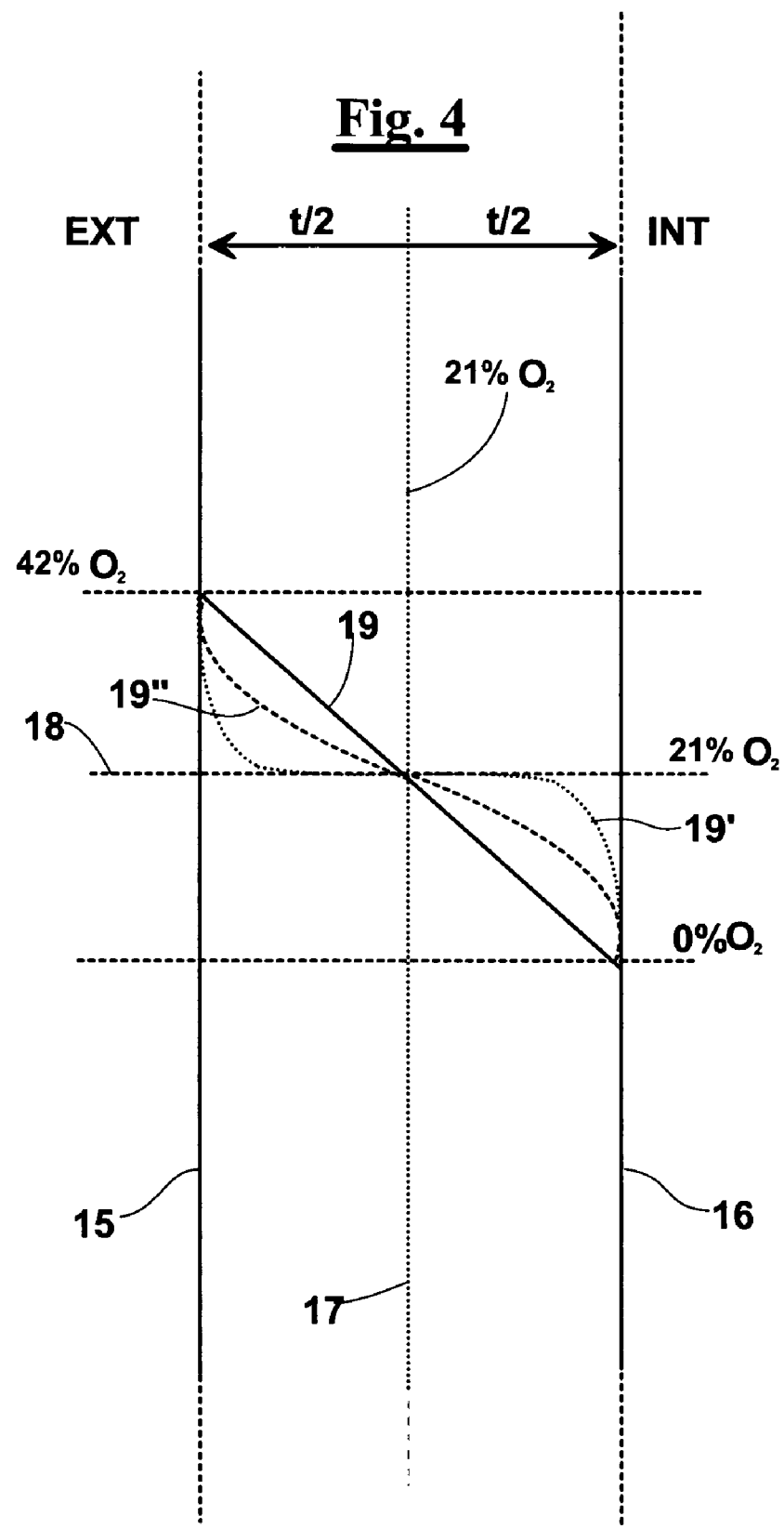

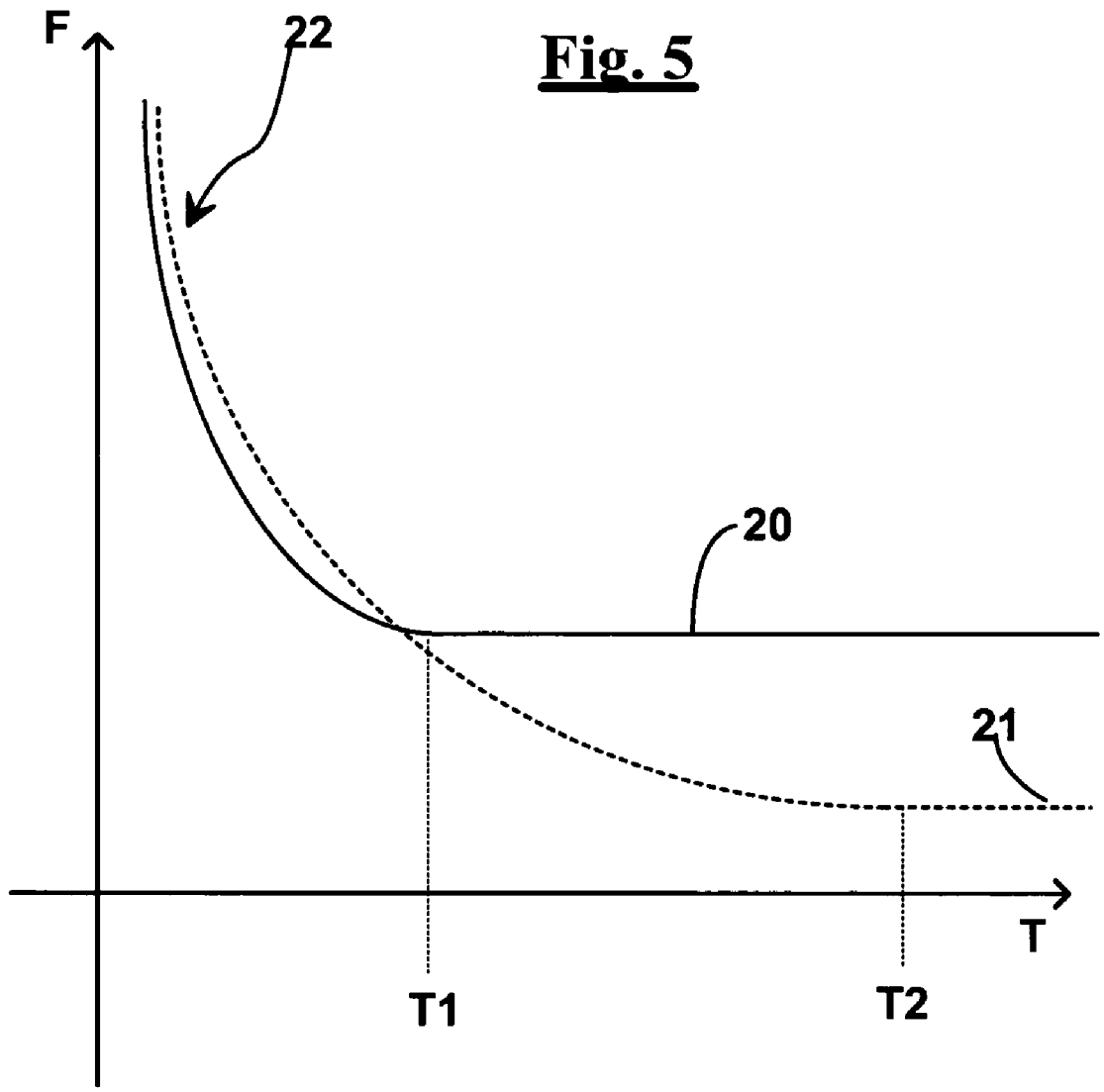

METHOD FOR MEASURING THE GAS PERMEABILITY OF CONTAINERS AND SEALING MEMBERS IN GENERAL

FIELD OF THE INVENTION

The present invention relates to a method for measuring gas permeability of containers in general, such as bottles, bags with various shapes or also membranes and other sealing elements such as caps.

BACKGROUND OF THE INVENTION

As well known, in the packaging industry, both for food and pharmaceutical applications, it is necessary to limit the permeability of the packages both to oxygen and to other gas species, to protect with time the quality of the contents.

A system for measuring permeability of containers to oxygen is described in US2005076705. In this document a description is given on how to measure with special sensors a volume variation of a gas permeated into the container, in two different instants and according to the perfect gas law. Then a described equation is integrated with time obtaining a volumetric variation of gas with time in the container. Before carrying out the two volumetric measurements, it is necessary to await the end of a transient phase with subsequent long and expensive waits.

In another common method a container to be analysed is put in a test chamber. In the test chamber the container is suitably sealed and insulated, except from an inlet duct and an outlet duct through which a gaseous carrier, normally nitrogen, is caused to flow into the container. In the test chamber, out of the container, a pure gas sample is delivered, normally oxygen or carbon dioxide, or a mixture comprising the gas carrier and the gas sample. The gas sample can permeate into the container through the walls of the container same. The gas carrier that flows in the container has a double function of maintaining in the container the same pressure as in the test chamber, normally atmospheric pressure, for balancing the forces and avoiding that the container collapses, as well as for carrying the permeated gas towards a sensing device for detecting its concentration.

The gas carrier that flows out from the container reaches a sensing device, normally an electrochemical cell or a infrared detector. The sensing device, once started the measure, reveals a variable concentration value of the permeated gas in the flow of the gaseous carrier. By keeping constant both the gas sample flow in the test chamber and the gas carrier flow in the container, the sensing device follows a chart that converges to a steady condition, i.e. a condition in which the permeated gas measured concentration is constant with time. The measured value, once converged, represents the gas flow permeating into the container i.e a value proportional to the permeability of the container.

The same method can be used for measuring the permeability of low permeability closure elements for containers, such as corks or caps. The container is arranged in the test chamber in a similar way as above described, sealed by the closure element. In the walls of the container inlet and outlet passages are artificially made, normally sealed with epoxy resin, for the flow of the gaseous carrier.

The problem of this system is the waiting time necessary for achievement of the convergence, which can in some cases be very long, for example for corks even for weeks, with consequent high process costs.

SUMMARY OF THE INVENTION

It is therefore a feature of the present invention to provide a method for measuring gas permeability of containers or of sealing elements that requires a measuring time that is much less than traditional techniques.

It is also a feature of the invention to provide a method for measuring the gas permeability of containers that does not require necessarily very sensitive and expensive sensors.

These and other objects are accomplished by a method according to the present invention for measuring permeability to a gas sample through a container or a sealing element, said container or said sealing element having an outer face, a thickness and a inner face, in said thickness a measured starting concentration of the gas sample being arranged, comprising the following steps:

exposition of the outer face to a flow of said gas sample mixed to other gas at a determined and fixed concentration;

exposition of the inner face to a flow of a gas carrier, at a determined and fixed concentration;

contact of the inner face with said gas carrier measuring the gas sample actually permeated and conveyed by said gas carrier;

awaiting a steady condition of the measured actual permeated gas value, an considering said measured value as permeability of the container or sealing element to the gas sample;

characterised in that:

said measured and fixed concentration of the gas sample to which said outer face is exposed is chosen such that the difference between the concentration of the gas sample to which said outer face is exposed and said gas sample starting concentration in said thickness is substantially equal to the difference between the gas sample starting concentration in said thickness and an expected concentration of gas sample to which said inner face is exposed, where the gas sample starting concentration in said thickness is calculated by assuming a solubility coefficient close to 1.

In other words, by assuming a solubility coefficient close to 1 of the gas sample in the material, if in the thickness of the container the starting concentration of the gas sample is equal to X, and in the container the concentration of the gas sample is $X_0$, then, according to the invention, the concentration of the gas sample out of the container is equal to $2(X-X_0)$. This way, after convergence, the profile of concentration of the gas sample, in the thickness between the outer and the inner face is substantially a linear decrease with average value falling on the middle line of the thickness and equal to starting value X. Thus, the migration of the gas sample is apportioned for half thickness respectively between the outer and the middle line and between the middle line and the inner line, thus reducing remarkably the migration time, and then the convergence time.

Advantageously, if said inner face is exposed to a pure gaseous carrier, with total absence of gas sample, said measured and fixed concentration of the gas sample to which said outer face is exposed is suitably chosen as substantially double the gas sample starting concentration in said thickness.

In particular, when measuring permeability to oxygen of said containers, the ratio of oxygen present in said insulated test chamber is set between 40 and 44%, and, in particular, is equal to 42%, being in this case the gas ratio of all the cross section of the element to be analysed in the starting condition set between 20 and 22%, and, in particular, substantially 21%, being this the concentration of oxygen present in air. This occurs if the solubility coefficient of oxygen in the material of the container is advantageously assumed to be close to 1. Actually, the concentration of oxygen in the material is proportional to this value responsive to the solubility coefficient, normally always much lower than 1. The choice of a solubility coefficient close to 1 is carried out exclusively for ease of calculation.

According to the invention, the concentration of the gas sample in the starting condition is kept at a fixed value at the middle plane between said outer face and said inner face. In particular, in case of oxygen as gas sample, said fixed value at the middle plane is set between 20 and 22%, and, in particular, is substantially 21%.

BRIEF DESCRIPTION OF THE DRAWINGS

Further characteristic and advantages of the method according to the present invention will be made clearer with the following description of an embodiment thereof, exemplifying but not limitative, with reference to the attached drawings, in which like reference characters designate the same or similar parts, throughout the figures of which:

FIG. 4 shows diagrammatically the cross sectional view of a container to be analysed during the step of permeation of the gas by the method according to the invention;

FIG. 5 shows in detail a comparison of a chart of the gas flow that permeates with time through the cross section of the container according to the invention and according to the prior art.

DESCRIPTION OF PREFERRED EXEMPLARY EMBODIMENTS

Figure 1:
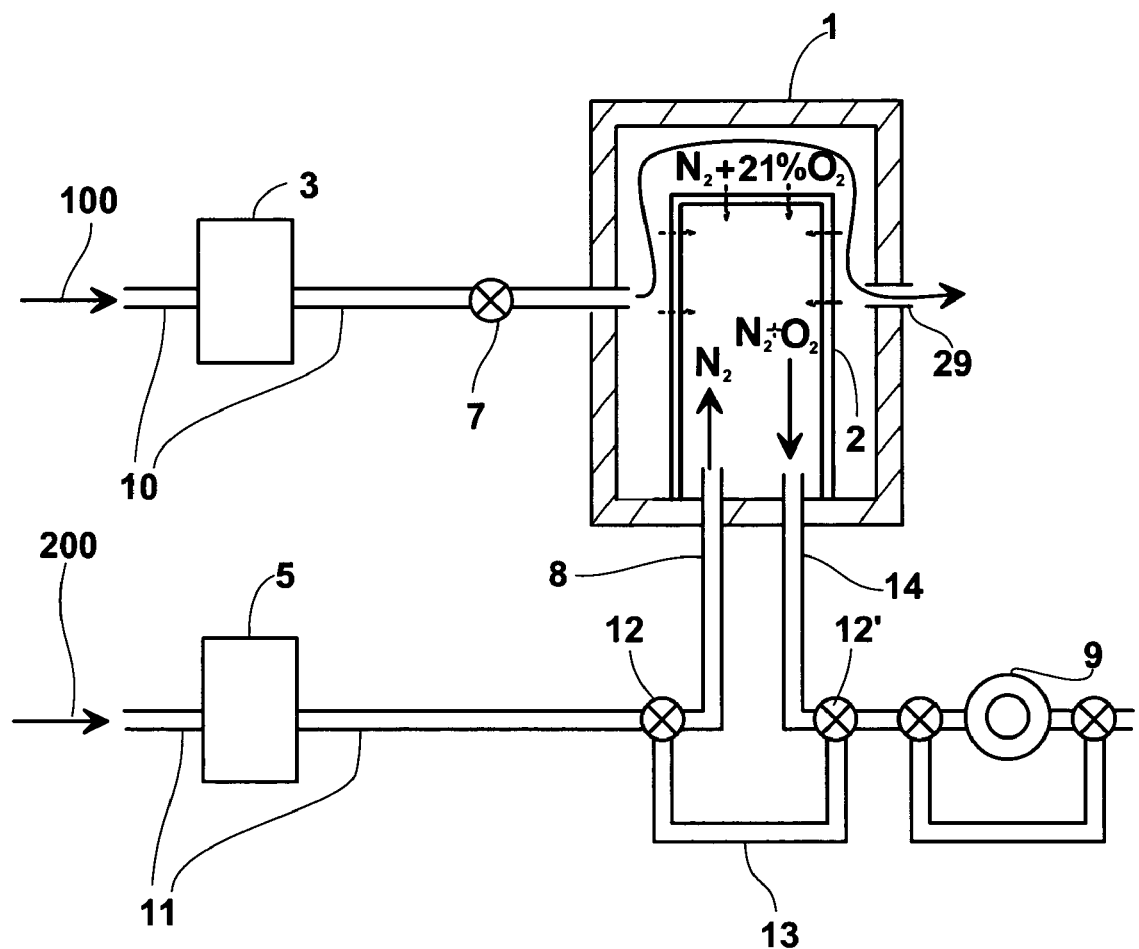
FIG. 1 shows diagrammatically a perspective view of a device for carrying out a gas permeability test by a known method.

In the following description and in the drawings reference has been always made to a solubility of the gas sample in the material close to 1. Actually the solubility of the gas sample in the material is always much less than 1. However, it is not necessary to know the actual solubility, since the advantages of the method according to the invention are unchanged.

With reference to FIG. 1, a system configuration is described for executing a method for measuring permeability to oxygen of containers such as bottles, bags or sealing elements in general such as membranes or caps. According to the prior art, a generic container 2, for example a bottle made of a material whose permeability has to be measured, for example a paper, plastic, cork material, etc., is arranged in a insulated test chamber 1.

Test chamber 1 is connected to an air duct 10 and connected to a gas-mass regulator indicated as 3. Regulator 3 has the object of feeding a constant flow of gas, in this case air, delivered in chamber 1 during the permeability test. A duct 11 instead feeds another gas different from oxygen, in particular, nitrogen $N_2$, or also hydrogen or helium or a mixture thereof, which runs in duct 11 as gaseous carrier.

The gaseous carrier, through a gas-mass regulator 5, reaches container 2 through a duct 8 arranged between duct 11 and chamber 1. Between duct 11 and duct 8 a valve 12 is arranged adapted to switch the flow between chamber 1 and a bypass 13, which ends in an outlet duct 14 for gaseous carrier, through valve 12'. Bypass 13 has the function of adjusting the "zero", necessary for evaluating the possible presence of traces of oxygen already present in the gaseous carrier, for example for insufficient purity or for the presence of leaks in the device, and not due to the permeability of the material examined. This adjustment is carried out only by feeding the gaseous carrier, without that it comes into contact with chamber 1.

The gaseous carrier, in particular, $N_2$, mixes with the gas to measure, in particular, $O_2$, permeated through container 2 and indicated by the small arrows. Then, through outlet duct 14 it reaches measuring sensor 9, in particular, a electrochemical cell or infrared detector.

Figure 2:
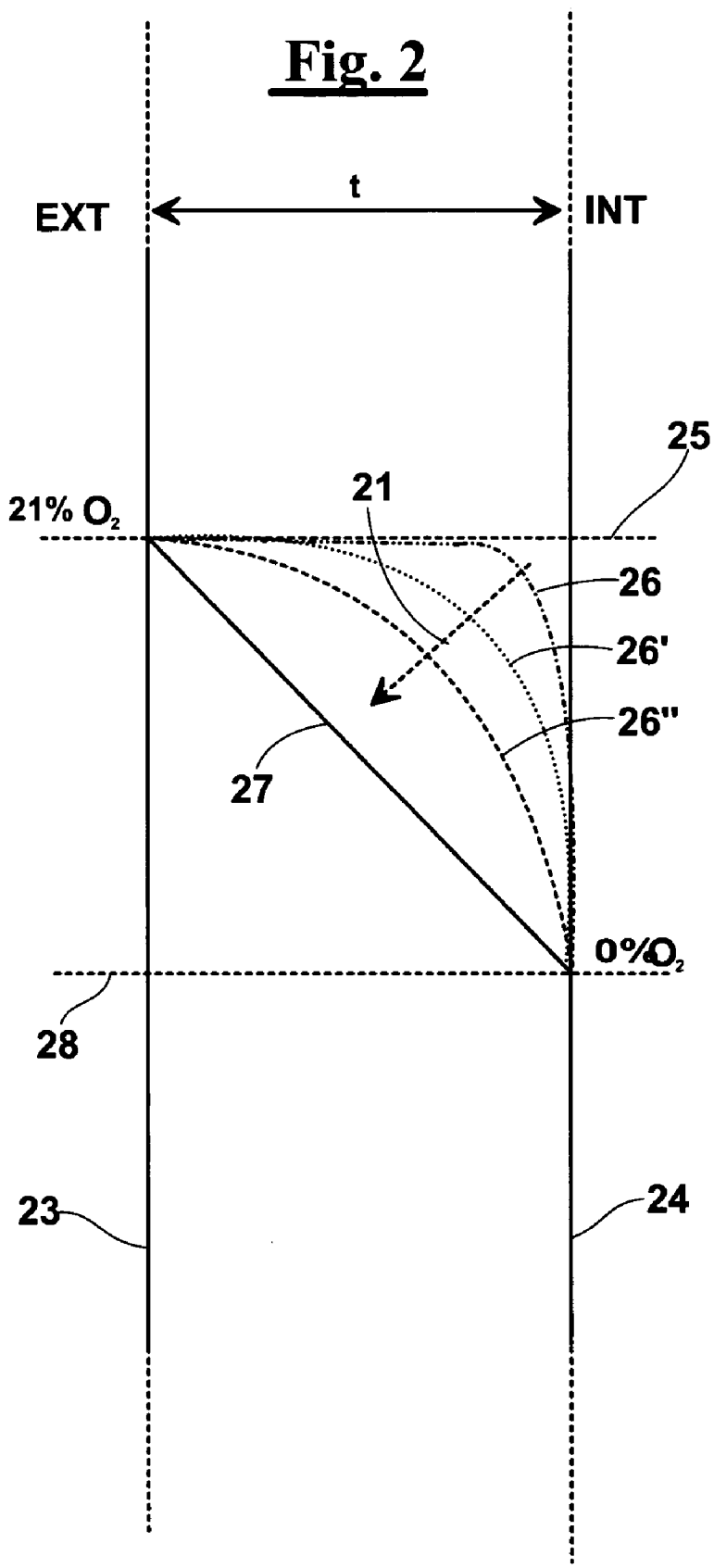
FIG. 2 shows a transient phase of the permeation through a wall cross section of a container to be analysed having a generic thickness whose external surface comes into contact with air.

The transient phase of the permeation through the wall of container 2, of generic thickness t, is shown in FIG. 2, which represents a cross sectional view of the wall of the container to be analysed whose external surface 23 comes into contact with air, i.e. as well known a mixture of gas with 21% oxygen present in the test chamber, whereas the inner surface comes into contact with the only gas carrier and therefore with absence (0%) of oxygen.

Before being put in the test chamber, the container has been immersed in air, and then, in the calculated case of solubility coefficient close to 1, it is in conditions steady balance at 21% of oxygen, indicated by line 25, in all its thickness t. Otherwise the ratio of oxygen depends on the solubility coefficient of oxygen in the material of the container.

Once put in the test chamber, and once started the outer flows of gas or mixture permeating into the container and the inner flow of gas carrier, thickness t is affected by the difference of ratio of oxygen defined by the presence of 21% oxygen on the external surface 23 and by the 0% of oxygen on its inner surface 24. With time, thickness t will tend to achieve a configuration of equilibrium. While external wall 23 is actually already in a condition of balance with the environment, when moving towards inside wall 24 each longitudinal cross section along said thickness t of said cross section will have to release oxygen for turning into in a condition of balance applied on inner surface 24. The transient phase phenomenon develops towards of arrow 21 according to curves 26', 26" shown in FIG. 1, i.e. at the beginning the gas carrier will wash the oxygen present in the innermost longitudinal sections, and then, eventually, the gas carrier will wash also the outermost longitudinal sections. Curves 26', 26' show this transient phase with variable oxygen flow with time up to the achievement of the steady condition of constant flow, shown instead by a line 27 with fixed slope. Only at this point sensor 9 of FIG. 1 measures in steady condition a flow of oxygen permeated through the container.

As above said, the waiting time necessary for an achievement of said steady condition can be very long. Furthermore, for small containers, being small the amount of oxygen that permeates, the measure is troublesome using sensors that are very sensitive and expensive.

Following the method according to the invention, chamber 1 is crossed, out of the container 2, by a flow of nitrogen and oxygen, with oxygen at a ratio of 42%, as indicated in FIG. 4. At the same time, by duct 8 running into container 2 a flow nitrogen is introduced.

Normally at the end of the test a zero setting is carried out for the stated previously reasons. This is carried out by operating valves 12 and 12' that act as opening and closing tap. This way it is possible to cause the gaseous carrier to flow towards sensor 9 together with the possible impurities of oxygen present in it. For executing an actual measure said bypass is set in a way suitable to insulate duct 13 and to allow the onset of the flow in wrapper 2.

FIG. 4 describes such an operation, representing a cross sectional view of container 2 having an external surface 15 that contacts the mixture of nitrogen and oxygen and an inner surface 16 that contacts the nitrogen. At the beginning of the measure that is done according to the invention, sensor 9, by said duct 14 according to the direction of arrow B, shown in FIG. 1, will detect a very high flow of oxygen transported by the gaseous carrier, in particular, nitrogen, and it will decrease quickly with time. This high flow is due to degassing, i.e. removal of oxygen originally present in container 2.

FIG. 5 indicates in fact as 22 the portion of flow decreasing quickly with time according to the present invention coincident also with what happens in the prior art. Then the flow will decrease, but a transient phase will still be present with a flow unsteady with time. In order to actually measure the real permeability of the container to oxygen it is necessary to await a time when the flow is fixed.

Always in FIG. 5 a time T1 and T2 necessary to achieve a fixed flow are in fact indicated respectively according to the invention and according to the prior art. In fact, as depicted in FIG. 4 by balance curves 19, 19' and 19", it is shown how the various sections of the container tend to achieve the balance with time. In particular, in a starting condition all the cross section of said container will contain a ratio of gas at 21%, as indicated by horizontal line 18. Therefore, as soon as said cross section is put into contact with oxygen at a 42% ratio in its external surface and at 0% in its inner surface, said cross section will tend to achieve a condition of balance according to said curves 19' and 19" with time, up to the final balance condition shown by line 19 having a fixed slope and reached after said time T1 of FIG. 4. In other words the counterpart of the thickness external to the 21% line will tend to accept oxygen for reaching the condition of 42% balance applied by the outer environment of insulated test chamber 1, whereas the inner counterpart 16 of the thickness will loose oxygen for moving to the limit condition of 0% applied in said container. Therefore an axis of symmetry 17 is defined in the thickness of container 2 that is constantly kept at a 21% ratio of sample gas. Therefore the two thickness counterparts t/2 tend towards their respective balance independently. In fact, the particular 42% oxygen ratio applied to insulated test chamber 1 is exactly double of that actually present in all the thickness before starting the test. This is equivalent to the fact that the algebraic difference between the ratio of oxygen that is constant in insulated test chamber 1 and the ratio of oxygen in thickness t at the beginning of the test is equal to the algebraic difference between the ratio of oxygen present in said cross section at the beginning of the test and that present within the bottle, i.e. 0%. This creates therefore the symmetry shown in FIG. 4 with respect to said axis 17 and the fact that the two parts of said cross section tend to the balance independently and at the same time. Since the time necessary to achieve the status of steady flow shown by curve 19, as well known in the literature, depends on the square of the cross section thickness, then a balance achieved in half cross section causes the convergence time to be reduced to a quarter.

Without any limitation the same test can be carried out with a gas different from oxygen and nitrogen, simply considering an axis of symmetry of the material to be analysed by setting a percentage of gas sample in said insulated test chamber 1 double the percentage in the whole cross section before the beginning of the test. Naturally, the amount of gas sample different from oxygen present at first in said cross section of the container has to be known and set with a kind of preconditioning of said container, for example putting it in an environment with said gas for a predetermined time.

Figure 3:
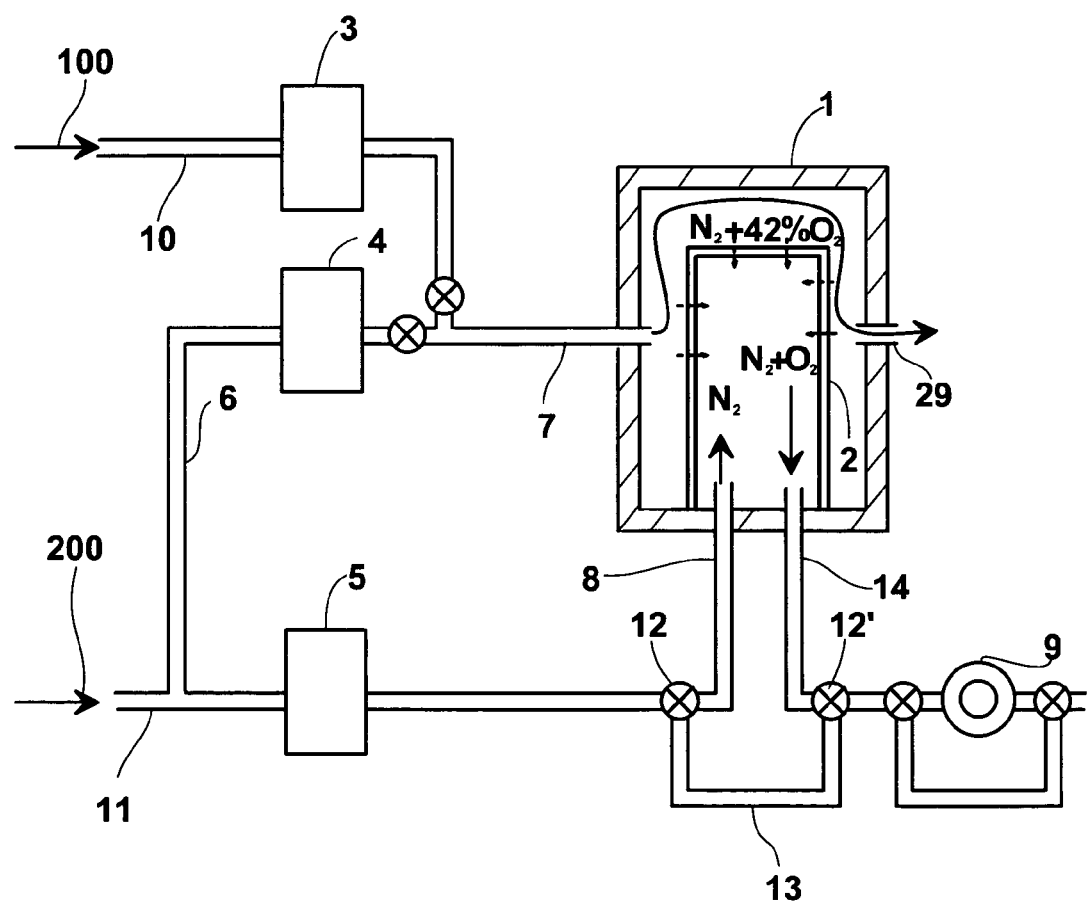
FIG. 3 shows diagrammatically a perspective view of the device for carrying out a gas permeability test by a method according to the invention.

FIG. 3 shows one embodiment of a device that carries out the method according to the invention, comprising an inlet duct for a gaseous carrier, in particular, nitrogen, having the function both as inlet into container 2 and as inlet into chamber 1 and around container 2 whose permeability has to be measured. The duct that enters into container 2 comprises tubes 11 and 8, whereas, the duct that exits from container 2 comprises tubes 6 and 7. Such ducts have an origin in common in order to allow the distribution among them of the flow 200 of gas carrier as input. An inlet duct is provided 10 for a sample gas flow, such as oxygen, which ends into duct 7 to be mixed with the gas carrier in chamber 1. A gas-mass regulator is provided for each inlet duct, respectively indicated as 5, 4 and 3.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. A method for measuring the permeability of a sample gas through a container or a sealing element, said container or said sealing element having an outer face, an inner face, and a thickness containing a measured starting concentration of the sample gas, said method comprising the steps of:
   exposing the outer face of said container or sealing element to a fixed flow rate of said sample gas;
   exposing the inner face of said container or sealing element to a flow rate of carrier gas, said carrier gas being different from said sample gas;
   contacting the inner face with said carrier gas and measuring the sample gas that has permeated through said container or sealing element and is conveyed by said carrier gas;
   awaiting a steady condition of measured permeated gas value, whereby said measured permeated gas value represents the permeability of the container or sealing element to the sample gas;
   whereby said method is further characterized in that:
   a) said concentration of the sample gas to which said outer face is exposed is chosen such that the difference between the concentration of the sample gas to which said outer face is exposed and said sample gas starting concentration in said thickness is substantially equal to the difference between (a) the sample gas starting concentration in said thickness and (b) an expected concentration of sample gas to which said inner face is exposed, wherein the sample gas starting concentration in said thickness is calculated by assuming a solubility coefficient close to 1.

2. A method, according to claim 1, wherein said inner face is exposed to substantially pure carrier gas, and the concentration of the sample gas to which said outer face is exposed is double the sample gas starting concentration in said thickness.

3. A method, according to claim 1, wherein, when measuring permeability of an insulated test container to oxygen, the ratio of oxygen present in said insulated test container, is between 40 and 44%.

4. A method, according to claim 3, where the sample gas concentration in said thickness of said container or sealing element to be analyzed at a starting condition is between 20 and 22%.

5. A method, according to claim 3, where the gas ratio in all the cross section of the element to be analyzed in the starting condition is set to about 21%.

6. A method, according to claim 1, where the concentration of the sample gas in a starting condition is at a fixed value in said thickness of said container or sealing element at a middle plane between said outer face and said inner face.

7. A method, according to claim 6, wherein said sample gas consists essentially of oxygen and the fixed value at the middle plane is set between 20 and 22%.

8. A method, according to claim 1, wherein, when measuring permeability of said containers to oxygen the ratio of oxygen present in said insulated test chamber is set to about 42%.

9. A method, according to claim 1, wherein, in case of oxygen as gas sample, the fixed value at the middle plane is set to about 21%.

* * * * *